United States Patent [19]
Weinstein et al.

[11] Patent Number: 6,051,585
[45] Date of Patent: Apr. 18, 2000

[54] SINGLE-DOSE ANTIHISTAMINE/ DECONGESTANT FORMULATIONS FOR TREATING RHINITIS

[76] Inventors: Robert E. Weinstein, 177 Commonwealth Ave., Boston, Mass. 02116; Alan M. Weinstein, 9205 Pegasus Ct., Potomac, Md. 20854

[21] Appl. No.: 09/206,713

[22] Filed: Dec. 7, 1998

[51] Int. Cl.⁷ .................................................. A61K 31/44

[52] U.S. Cl. ............................ 514/335; 514/849; 514/853

[58] Field of Search ...................................... 514/335, 849, 514/853

[56] References Cited

U.S. PATENT DOCUMENTS 5,314,697  5/1994  Kwan et al. .............................. 424/480

OTHER PUBLICATIONS

Bronsky et al. *The Journal of Allergy and Clinical Immunology* Aug. 1995, 96(2), 139–147.

*Primary Examiner*—Kathleen K. Fonda
*Attorney, Agent, or Firm*—Robert R. Deleault, Esq.; Mesmer Law Offices, P.A.

[57] ABSTRACT

An oral once-per-day single dosage unit for treating the symptoms of rhinitis expertly formulated with a nasal decongestant and antihistamine. Preferably, the antihistamine is non-sedating.

13 Claims, No Drawings

SINGLE-DOSE ANTIHISTAMINE/DECONGESTANT FORMULATIONS FOR TREATING RHINITIS

BACKGROUND OF THE INVENTION

1. Field of the Invention

The present invention relates to treatments for rhinitis, more particularly, to combinations of decongestant and non-sedating antihistamine that avoid stimulation when stimulation is not desired.

2. The Prior Art

Rhinitis refers to an inflammatory disorder of the nasal passages. The symptoms of rhinitis typically consists of sneezing, rhinorrhea, nasal congestion, and increased nasal secretions. Failure of treatment of rhinitis may lead to other disorders which include infection of the sinuses, ears, and lower respiratory tract.

Two types of oral medication are commonly used to treat the symptoms of rhinitis: decongestants and antihistamines. Decongestants and antihistamines differ in their mechanisms of action, therapeutic effects, and side effects. It is common practice to combine both of these medications to bring about more complete symptom relief of rhinitis than with either entity alone.

Decongestants commonly used to treat rhinitis include the adrenaline-like agents pseudoephedrine and phenylpropanolamine. These agents act to constrict vessels in the nasal mucus membranes and thereby decrease tissue swelling and nasal congestion. Decongestants, are found to be better than antihistamines for restoring the patency of congested nasal airways. Like adrenaline, nasal decongestants are stimulatory and produce side effects which may be tolerated while the user is awake, and may even be considered desirable to counter fatigue which is known to accompany other symptoms of rhinitis. Decongestants, however, may produce nervousness, restlessness, and insomnia if taken when sleep is desired. This can be a source of confusion for individuals, who mistakenly attribute their inability to sleep to the malaise which may accompany other rhinitis symptoms, rather than to the decongestant medication.

Histamine is a mediator released from cells which line the walls of the nasal mucous membranes (mast cells). When released, histamine binds to local histamine receptors, thereby causing sneezing, nasal itching, swelling of the nasal membranes, and increased nasal secretions. Antihistamines relieve these effects, albeit by a different mechanism than decongestants. Antihistamines block the binding of histamines to the histamine receptors by preemptively binding to the receptors. Consequently they are effective only if given prior to histamine release since once histamine is released and binds to the receptors, it is too late. Although individuals typically take antihistamines after symptoms occur, it is more desirable to dose antihistamines so as to effect therapeutic availability in anticipation of histamine release.

Antihistamines are generally sedating. However, newer antihistamines with no or little sedation have been developed in the last twenty years.

Combining decongestants and antihistamines utilizes both mechanistic approaches, and has been shown to offer more complete relief of rhinitis symptoms than therapy with either component alone. Consequently, many products have been formulated so that their dosage units contain both. The incorporation of decongestant and sedating antihistamine into a single dosage unit attempts a balance between the stimulating and sedating side effects of these components. However, individuals are known to vary in their susceptibility to these side effects. Consequently, some individuals experience stimulation and insomnia when taking these combinations at night. More recently, formulations have been commercialized which incorporate a decongestant and a non-sedating antihistamine into a single dosage unit for the purpose of avoiding daytime sedation. Such combinations might be expected to provoke a greater incidence of nighttime irritability and insomnia because the stimulating side effects of decongestant are not attenuated by concomitant sedation by antihistamine. Indeed, a 25% incidence of insomnia has been disclosed among users of a commercialized combination of the non-sedating antihistamine terfenadine and the decongestant pseudoephedrine. Examples of such formulations include:

SELDANE-D® Extended-Release Tablets which contains 60 mg terfenadine (non-sedating antihistamine) and 120 mg pseudoephedrine hydrochloride (stimulating decongestant), and which is recommended to be taken every 12 hours (adults and children over 12 years of age).

ALLEGRA-D® contains 60 mg fexofenadine (non-sedating antihistamine) and 120 mg pseudoephedrine hydrochloride (stimulating decongestant), and which is recommended to be taken every 12 hours (adults and children over 12 years of age).

CLARITIN-D® 24-HOUR Extended-Release Tablets which contains 10 mg loratidine (non-sedating antihistamine) and 240 mg pseudoephedrine hydrochloride (stimulating decongestant), and which is recommended to be taken every 24 hours (adults and children over 12 years of age).

These and all currently marketed single entity combinations which are formulated with decongestant and non-sedating antihistamine fail to address the problem of nighttime irritability and insomnia, a problem which is increased by combining non-sedating, rather than sedating antihistamine.

Note is made of prior art which is directed toward reducing the side effects of antihistamines and decongestants. U.S. Pat. No. 4,295,567, issued to Knudsen, teaches a regimen for employing separate day and night dosage units for the purpose of avoiding daytime sedation from sedating antihistamines. This patent does not anticipate the advent of non-sedating antihistamine and overlooks the side effect of nighttime stimulation from decongestants. A regimen, commercialized as SYN-RX™, also employs separate day and night dosage units. SYN-RX™ contains a daytime formulation of 600 mg guaifenesin, which is non-stimulating, and 60 mg pseudoephedrines, which is stimulating, and a nighttime formulation of 600 mg of guaifenesin alone. SYN-RX™ does not contain an antihistamine. In failing to contain any medication which would be effective for the symptoms of rhinitis at night, SYN-RX™ does not constitute a treatment for rhinitis. The use of multidosage unit regimens of such prior art is less convenient for a user than a single dose, once-per-day formulation, and more complex to follow, adding the potential for a user to confuse dosage units.

Individuals with rhinitis utilize antihistamines and decongestants together many of millions of times a year. Professional as well as consumer confusion is widely encountered with the use of these medications together, and unnecessarily negative consequences occur both by self-selection and prescription. In particular, individuals treated with decongestants at night not only risk insomnia, but also daytime irritability, fatigue, and malaise from lack of rest. It is known that these side effects are sometimes mistakenly ascribed to rhinitis rather than to the medication causing them. There is a present need for formulations which circumvent this confusion and which avoid nighttime stimulation.

SUMMARY OF THE INVENTION

It is an object of the present invention to simplify the combined use of antihistamine and nasal decongestant medications for a user for the purpose of enhancing the convenience of utilizing these medications, reducing error in taking these medications, and reducing the side effects of these medications.

Another object is to formulate antihistamines and decongestants together for the treatment of rhinitis so as to avoid stimulation at night.

Yet another object is to provide a formulation for a user which incorporates antihistamines and decongestants together as a single dosage unit for the treatment of rhinitis in a manner so as not to cause stimulation at night and which can be taken once per day.

A further object is to provide a user with a single dosage unit which provides an operational combination of decongestant and antihistamine during the day and antihistamine without decongestant at night.

The single dosage unit of the present invention for treating the symptoms of rhinitis is expertly formulated with a combination of medications, including a nasal decongestant, antihistamine, and optionally, other medications, such as an analgesic. The dosage unit is for oral ingestion. The dosage unit preferably contains a non-sedating antihistamine, such as loratidine, cetirizine, or fexofenadine. Examples of decongestants include pseudoephedrine and phenylpropanolamine.

Other objects of the present invention will become apparent in light of the following detailed description of the invention.

DETAILED DESCRIPTION

The single dosage unit of the present invention for treating the symptoms of rhinitis contains a combination of medications which include nasal decongestants and antihistamines. The dosage units may be in the form of tablets, pills, capsules, caplets, or other recognized oral form of medication. The dosage unit may be formulated to contain sedating or, preferably, non-sedating antihistamine. The components are formulated so as to produce the pharmacokinetic and therapeutic characteristics desired. The devising of such formulations requires pharmaceutical expertise and requires understanding of the actions, side effects, and pharmacokinetics of antihistamines, decongestants, components which affect the bioavailability of the medications, and other formulated components.

The terms "day" and "night" used herein are intended to be synonymous with the period of wakefulness, when stimulation might be acceptable, and the period of sleeping, when stimulation would be undesired, respectively. Such times vary in accordance with the schedule of individuals.

Examples of the preferred single dosage units of the present invention include:

EXAMPLE 1

A single dosage unit consisting of 120 mg pseudoephedrine, a stimulating decongestant, prepared so as to be released over a 12-hour time period, and 10 mg loratidine, a non-sedating antihistamine, formulated so as to be released immediately. When taken at the start of the day (a time anticipating a desire to be awake for 12 to 16 hours), this dosage unit provides immediate dosing with loratidine, which is known to exert an antihistaminic effect 1 to 3 hours after dosing, reach a maximum at 8 to 12 hours, and last in excess of 24 hours. This dosage unit [also] preferably provides immediate and delayed [bioavailability of] action of pseudoephedrine [over a 12-hour period], so as to exert an effect during daytime hours, when stimulation of pseudoephedrine is best tolerated, but not at night. Once released, pseudoephedrine has a 4 to 6 hour half-life, considerably shorter than that of loratidine. The comparatively short decongestant effect of pseudoephedrine may be prolonged by release over time so as to achieve efficacy through the waking hours, but not during the time when stimulation is undesired. Time-release methods to prolong the duration of action after dosing are well known in the art. One such method involves the additional formulation of cellulose ether base materials such as hydroxypropyl methylcellulose to bond to the therapeutic agent and delay its bioavailability. Such time-release methods may be utilized to delay the bioavailability of all or only a portion of the ingested dose, and for varying lengths of time. The antihistamine and decongestant components of this formulation are similar to that of CLARITIN-D® 24-HOUR Extended-Release Tablets which contains 10 mg loratidine (antihistamine) and 240 mg pseudoephedrine hydrochloride (decongestant), and which is recommended to be taken every 24 hours in adults. The present invention formulation differs, however, in that it contains a lesser dose of pseudoephedrine, and that it limits the duration of action of pseudoephedrine to the daytime hours, thereby avoiding the stimulation of pseudoephedrine at night.

EXAMPLE 2

A single dosage unit consisting of 75 mg phenylpropanolamine, a stimulating decongestant, prepared so as to be released over a 12-hour time period, and 10 mg cetirizine, a non-sedating antihistamine, prepared so as to be released immediately. When taken at the start of the day, this formulation provides immediate dosing with cetirizine, which is known to exert an antihistaminic effect within one hour after dosing and to persist for at least 24 hours. This formulation also preferably provides immediate and delayed action of phenylpropanolamine over a 12-hour period [not in excess of 16 hours after administration], so as to exert effect during daytime hours, when its stimulation is best tolerated, but exerts no effect at night. Like pseudoephedrine, the comparatively short half-life and decongestant effect of phenylpropanolamine, is prolonged in this formulation by incorporating a prolonged release of phenylpropanolamine over time so as to achieve efficacy through the waking hours, but not so long as to provide phenylpropanolamine activity during the time when stimulation is undesired.

EXAMPLE 3

A single dosage unit consisting of 75 mg phenylpropanolamine, a stimulating decongestant, prepared so as to be released over a time period, and 120 mg of fexofenadine, a non-sedating antihistamine, prepared so as to be active over a 24-hour period. Fexofenadine, when given alone, is known to exhibit antihistaminic effect within one hour, achieves a maximum effect at 12 hours, and still has a visible effect at 24 hours. This formulation preferably provides immediate and delayed activity of fexofenadine over a 24-hour span. This formulation also preferably provides immediate and delayed action of phenylpropanolamine over a 14-hour period [not in excess of 16 hours after administration], so as to exert an effect during daytime hours, when stimulation is best tolerated, but not so long as to provide an effect during the time when stimulation is undesired, as at night.

In addition to antihistamines and decongestants, additional therapeutic ingredients for the treatment of rhinitis may be formulated if desired. For example, analgesics such as salicylates and acetaminophen may be considered for inclusion in such dosage unit, and are within the scope of this invention.

These examples do not constitute an exhaustive list of potential combinations, and variations and modifications may be made by those of ordinary skill in the art. Those of skill in the art may also recognize modifications to these presently disclosed embodiments. One such modification might involve a time-release of decongestant over periods other than those exemplified, but not so as to allow stimulation at night. These variations and modifications are meant to be covered by the spirit and scope of the present claims.

Thus it has been shown and described antihistamine/decongestant formulations for treating rhinitis which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A once-per-day single oral dosage unit comprising:
   (a) a decongestant formulation having a duration of action of no more than about 16 hours; and
   (b) an antihistamine.

2. The dosage unit of claim 1 wherein said decongestant is pseudoephedrine.

3. The dosage unit of claim 1 wherein said decongestant is phenylpropanolamine.

4. The dosage unit of claim 1 wherein said antihistamine is non-sedating.

5. The dosage unit of claim 1 wherein the duration of action of said decongestant formulation is from about 12 hours to about 16 hours.

6. The dosage unit of claim 5 wherein the duration of action of said decongestant formulation is about 16 hours.

7. The dosage unit of claim 1 wherein the duration of action of said antihistamine formulation is about 24 hours.

8. The dosage unit of claim 1 wherein said decongestant formulation is immediately released upon ingestion.

9. The dosage unit of claim 1 wherein said decongestant formulation is time-released.

10. The dosage unit of claim 1 wherein said antihistamine formulation is immediately released upon ingestion.

11. The dosage unit of claim 1 wherein said antihistamine formulation is time-released.

12. A method of making a single oral dosage unit for treating rhinitis, said method comprising the steps of:
   (a) formulating a quantity of decongestant to have a duration of action of less than about 16 hours in a human;
   (b) formulating a quantity of antihistamine to have a duration of action greater than about 22 hours in a human; and
   (c) combining said formulated quantity of decongestant and said formulated quantity of antihistamine into a single oral dosage unit.

13. The method of claim 12 wherein said step of formulating a quantity of decongestant further includes formulating a quantity to have a duration of action of between about 12 hours to about 16 hours.

* * * * *